US012646600B2

(12) United States Patent
Sinha et al.

(10) Patent No.: US 12,646,600 B2
(45) Date of Patent: Jun. 2, 2026

(54) SYSTEM AND METHOD FOR PERFORMING INTERVENTIONAL PROCEDURES USING GRAPH NEURAL NETWORK MODEL

(71) Applicant: KONINKLIJKE PHILIPS N.V., Eindhoven (NL)

(72) Inventors: Ayushi Sinha, Baltimore, MD (US); Ashish Sattyavrat Panse, Burlington, MA (US); Grzegorz Andrzej Toporek, Cambridge, MA (US); Leili Salehi, Waltham, MA (US); Ramon Quido Erkamp, Swampscott, MA (US)

(73) Assignee: Koninklijke Philips N.V., Eindhoven (NL)

( * ) Notice: Subject to any disclaimer, the term of this patent is extended or adjusted under 35 U.S.C. 154(b) by 490 days.

(21) Appl. No.: 18/128,272

(22) Filed: Mar. 30, 2023

(65) Prior Publication Data

US 2023/0317227 A1 Oct. 5, 2023

Related U.S. Application Data

(60) Provisional application No. 63/325,770, filed on Mar. 31, 2022.

(51) Int. Cl.
*G16H 20/00* (2018.01)
*G06N 5/02* (2023.01)
(Continued)

(52) U.S. Cl.
CPC .............. *G16H 20/00* (2018.01); *G06N 5/02* (2013.01); *G06V 10/44* (2022.01); *G06V 10/82* (2022.01); *G16H 50/70* (2018.01)

(58) Field of Classification Search
None
See application file for complete search history.

(56) References Cited

U.S. PATENT DOCUMENTS

2016/0132648 A1 5/2016 Shah et al.

FOREIGN PATENT DOCUMENTS

CN 109635121 A 4/2019
CN 110911009 A 3/2020
(Continued)

OTHER PUBLICATIONS

Hou et al., "Multi-label learning with visual-semantic embedded knowledge graph for diagnosis of radiology imaging", IEEE, 9, 2021 pp. 15720-15730.
(Continued)

*Primary Examiner* — Fan Zhang

(57) ABSTRACT

A method and system are provided for performing an interventional procedure by a user on a subject. The method includes training a graph neural network (GNN) model using previous image data corresponding to previous images obtained during previous interventional procedures and corresponding previous treatment results, where the training causes the GNN model to provide a knowledge graph including feature representations and connections among the feature representations; receiving a feature representation of current image data corresponding to a current image showing a treatment target in the subject acquired by an imaging system; automatically identifying at least one next step of the interventional procedure by applying the feature representation of the interventional image data to the knowledge graph provided by the GNN model, where the at least one next step corresponds to at least one connection to at least one feature representation of the feature representations in the knowledge graph; and indicating to the user the at least one next step of the interventional procedure.

20 Claims, 3 Drawing Sheets

(51) Int. Cl.
    *G06V 10/44*         (2022.01)
    *G06V 10/82*         (2022.01)
    *G16H 50/70*         (2018.01)

(56)                 References Cited

FOREIGN PATENT DOCUMENTS

| CN | 111743574 A | 10/2020 |
|----|-------------|---------|
| CN | 112949728 A | 6/2021 |
| CN | 113205504 A | 8/2021 |
| CN | 113506622 A | 10/2021 |

OTHER PUBLICATIONS

Chen et al., "Label co-occurrence learning with graph convolutional networks for multi-label chest X-ray image classification", IEEE Journal of Biomedical and Health Informatics, 2019.

Sekuboyina et al., "A relational-learning perspective to multi-label chest X-ray classification" 2021.

Ramesh et al. "Zero-Shot Text-to-Image Generation". arXiv:2102.12092 (2021).

Chen et al., "Learning Semantic-Specific Graph Representation for Multi-Label Image Recognition". Proc. IEEE/CVF International Conference on Computer Vision (ICCV), pp. 522-531 (2019).

Nguyen et al. "Modular Graph Transformer Networks for Multi-Label Image Classification". Proc. AAAI Conference on Artificial Intelligence. 35(10): 9092-9100 (2021).

Choi et al., "Label Co-occurrence Learning with Graph Convolutional Networks for Multi-label Chest X-ray Image Classification", IEEE Journal of Biomedical and Health Informatics. 24(8): 2292-2302 (2020).

Rotmensch et al. "Learning a Health Knowledge Graph from Electronic Medical Records". Sci Rep 7, 5994 (2017). https://doi.org/10.1038/s41598-017-05778-z.

Choi et al., "Learning the graphical structure of electronic health records with graph convolutiona transformer." Proc. AAAI Conference on Artificial Intelligence. 34(01): 606-613 (2020).

SYSTEM AND METHOD FOR PERFORMING INTERVENTIONAL PROCEDURES USING GRAPH NEURAL NETWORK MODEL

CROSS-REFERENCE TO PRIOR APPLICATIONS

This application claims the benefit of U.S. Application No. 63/325,770, filed on Mar. 31, 2022. This application is hereby incorporated by reference herein.

BACKGROUND

The complexity and multitude of steps taken during different interventional procedures can make it difficult to assess what the best steps for a particular patient may be. Some patients may, for instance, be over-tested or under-tested which affects the downstream procedure plan for each patient, potentially assigning suboptimal procedure plans to patients. For instance, certain difficult or complicated procedure steps may be most beneficial only in a few complex cases, but not significantly beneficial to the general population undergoing a particular procedure. However, it may be hard to assess which patients require such procedure steps. Understanding a patient within the context of a population can help identify differentiating factors. However, the various factors that influence the complexity of a procedure combined with the large amounts of data generated during interventional procedures makes it difficult to mentally evaluate each patient within such a context.

Knowledge graphs have the ability to automate such evaluations through organized and efficient processing of medical data. The graph structure can help find patterns that affect clinical outcome and assist in decision making to improve clinical outcome. For diagnostic decision making, conventional solutions automatically build accurate knowledge graphs that show improved predictions for medication prescriptions using electronic health record (EHR) datasets. While learning structure from the EHR data or other text data is challenging, learning structure from interventional data collected during actual interventional procedures adds further challenges to this problem. Interventional data includes image data, which are larger and more difficult to process than sequential text. Interventional data may also include text and user interface (UI) interaction information, for example.

SUMMARY

According to a representative embodiment, a method is provided for performing an interventional procedure on a subject. The method includes training a graph neural network (GNN) model using previous image data from previous images obtained during previous interventional procedures and corresponding previous treatment results, where the training causes the GNN model to provide a knowledge graph including feature representations and connections among the feature representations; receiving a feature representation of current image data corresponding to a current image showing a treatment target in the subject acquired by an imaging system during the interventional procedure; automatically identifying at least one next step of the interventional procedure by applying the feature representation to the knowledge graph provided by the GNN model during the interventional procedure, where the at least one next step corresponds to at least one connection to at least one feature representation of the feature representations in the knowledge graph; and indicating to a user the at least one next step of the interventional procedure.

According to another representative embodiment, a system is provided for performing an interventional procedure on a subject. The system includes a database configured to store previous image data and unstructured procedure information corresponding to previous images obtained during previous interventional procedures and corresponding previous treatment results; an imaging system configured to acquire current images showing a treatment target in the subject during the interventional procedure; at least one processor; and at least one memory. The at least one memory stores instructions that, when executed, cause the at least one processor to train a GNN model using the previous image data and the unstructured procedure information and the corresponding previous treatment results from the database, where the training causes the GNN model to provide a knowledge graph including multiple feature representations and connections among the feature representations; receive a feature representation of current image data and current unstructured procedure information corresponding to the current images acquired by the imaging system during the interventional procedure; automatically identify at least one next step of the interventional procedure by applying the feature representation to the knowledge graph provided by the GNN model during the interventional procedure, where the at least one next step corresponds to at least one connection to at least one feature representation of the multiple feature representations in the knowledge graph; and indicate to the user the at least one next step of the interventional procedure.

A non-transitory computer readable medium storing instructions for performing an interventional procedure on a subject that, when executed by at least one processor, cause the at least one processor to train a GNN model using previous image data and unstructured procedure information corresponding to previous images obtained during previous interventional procedures and corresponding previous treatment results, where the training causes the GNN model to provide a knowledge graph including multiple feature representations and connections among the feature representations; receive a feature representation of current image data and current unstructured procedure information corresponding to a current image showing a treatment target in the subject acquired by an imaging system during the interventional procedure; automatically identify at least one next step of the interventional procedure by applying the feature representation to the knowledge graph provided by the GNN model during the interventional procedure, where the at least one next step corresponds to at least one connection to at least one feature representation of the feature representations in the knowledge graph; and indicate to the user the at least one next step of the interventional procedure.

According to another representative embodiment, a system is provided for performing an interventional procedure. The system includes a processor configured to: receive a model comprising a knowledge graph representing the interventional procedure by a plurality of feature representations and connections among the plurality of feature representations, the model configured to select a connection from among connections, corresponding to procedure steps of the interventional procedure, for a feature representation in the knowledge graph; identify a feature representation of a treatment target in a current image of a subject acquired during the interventional procedure; and apply the model to select a next procedure step in the interventional procedure based on the feature representation of the treatment target.

In an aspect, the processor is further configured to train the model, to generate the knowledge graph to represent the interventional procedure and to select from among connections for a feature representation in the knowledge graph, using previous image data, including treatment targets, from previous images obtained during previous interventional procedures and corresponding previous treatment results. In an aspect, the knowledge graph of the trained model includes a first feature representation corresponding to a current step in the interventional procedure and at least one connection from the first feature representation to at least one second feature representation corresponding to at least one possible next step in the interventional procedure; and the model is trained to select a connection of the at least one connection connected to a second feature representation corresponding to a best next step of the interventional procedure based on the treatment target.

In an aspect, the processor is further configured to train the model to assign weights to connections in the knowledge graph and to select from among the connections based on the assigned weights. In an aspect, the processor is further configured to train the model to select from among connections in the knowledge graph based on criteria associated with the interventional procedure. In an aspect, the criteria associated with the interventional procedure includes at least one of: size of the treatment target, location of the treatment target, type of the interventional procedure, procedural tools available for performing the interventional process, or previous classifications or outcomes of the interventional procedure using the procedural tools. In an aspect, the model is a graph neural network (GNN) model. In an aspect, the GNN model uses task-oriented outputs or reconstruction-oriented outputs to generate the plurality of feature representations in the knowledge graph.

In an aspect, the model is trained using at least one of: (i) previous unstructured procedure information corresponding to the previous images obtained during the previous interventional procedures and (ii) current unstructured procedure information corresponding to the current image. In an aspect, the model is trained using the previous image data and the previous unstructured procedure information comprises concatenating the previous unstructured procedure information to feature representations from the previous image data. In an aspect, the model is trained by condensing the previous image data to provide the plurality of feature representations and learning the connections among the plurality of feature representations using the previous image data and the corresponding previous treatment results.

In an aspect, the plurality of feature representations comprise at least one diagnostic feature representation of at least one pathological condition and at least one procedural feature representation for treating the at least one pathological condition during the interventional procedure. In an aspect, the system further comprises an imaging system configured to acquire the current image of the treatment target during the interventional procedure.

According to another representative embodiment, a method is provided for performing an intervention procedure. The method includes receiving a model comprising a knowledge graph representing the interventional procedure by a plurality of feature representations and connections among the plurality of feature representations, the model configured to select a connection from among connections, corresponding to procedure steps of the interventional procedure, for a feature representation in the knowledge graph; identifying a feature representation of a treatment target in a current image of a subject acquired during the interventional procedure; and applying the model to select a next procedure step in the interventional procedure based on the feature representation of the treatment target.

In an aspect, the method further comprises training the model, to generate the knowledge graph to represent the interventional procedure and to select from among connections for a feature representation in the knowledge graph, using previous image data, including treatment targets, from previous images obtained during previous interventional procedures and corresponding previous treatment results. In an aspect, the knowledge graph of the trained model includes a first feature representation corresponding to a current step in the interventional procedure and at least one connection from the first feature representation to at least one second feature representation corresponding to at least one possible next step in the interventional procedure; and the model is trained to select a connection of the at least one connection connected to a second feature representation corresponding to a best next step of the interventional procedure based on the treatment target.

In an aspect, the model is trained to assign weights to connections in the knowledge graph and to select from among the connections based on the assigned weights. In an aspect, the model is trained to select from among connections in the knowledge graph based on criteria associated with the interventional procedure. In an aspect, the criteria associated with the interventional procedure includes at least one of: size of the treatment target, location of the treatment target, type of the interventional procedure, procedural tools available for performing the interventional process, or previous classifications or outcomes of the interventional procedure using the procedural tools. In an aspect, the model is a graph neural network (GNN) model in which task-oriented outputs or reconstruction-oriented outputs are used to generate the plurality of feature representations in the knowledge graph.

BRIEF DESCRIPTION OF THE DRAWINGS

The example embodiments are best understood from the following detailed description when read with the accompanying drawing figures. It is emphasized that the various features are not necessarily drawn to scale. In fact, the dimensions may be arbitrarily increased or decreased for clarity of discussion. Wherever applicable and practical, like reference numerals refer to like elements.

DETAILED DESCRIPTION

Figure 1:
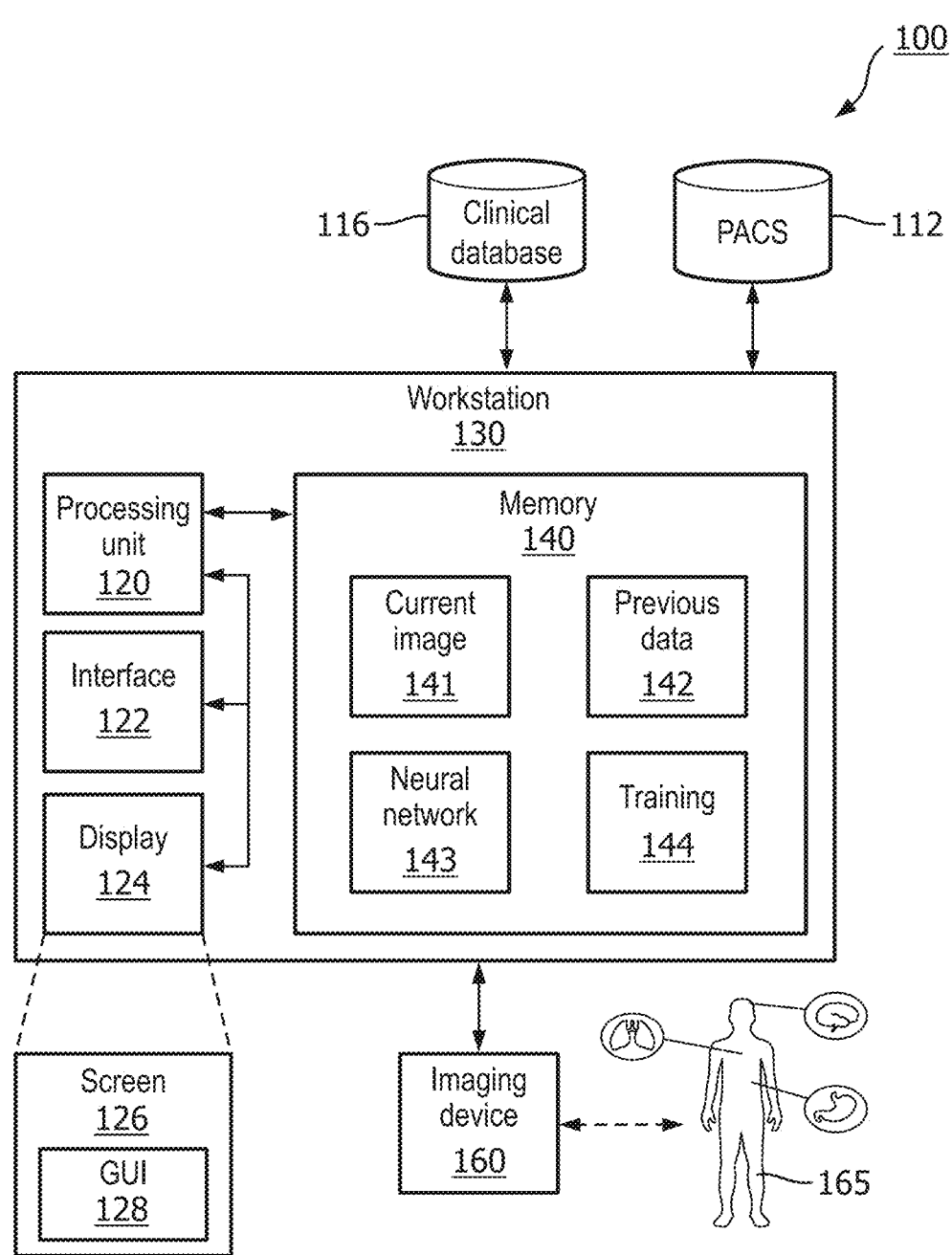
FIG. 1 is a simplified block diagram of a system for performing an interventional procedure on a subject, according to a representative embodiment.

In the following detailed description, for the purposes of explanation and not limitation, representative embodiments disclosing specific details are set forth in order to provide a thorough understanding of an embodiment according to the present teachings. Descriptions of known systems, devices, materials, methods of operation and methods of manufacture may be omitted so as to avoid obscuring the description of the representative embodiments. Nonetheless, systems, devices, materials and methods that are within the purview of one of ordinary skill in the art are within the scope of the present teachings and may be used in accordance with the representative embodiments. It is to be understood that the terminology used herein is for purposes of describing particular embodiments only and is not intended to be limiting. The defined terms are in addition to the technical and scientific meanings of the defined terms as commonly understood and accepted in the technical field of the present teachings.

It will be understood that, although the terms first, second, third, etc. may be used herein to describe various elements or components, these elements or components should not be limited by these terms. These terms are only used to distinguish one element or component from another element or component. Thus, a first element or component discussed below could be termed a second element or component without departing from the teachings of the inventive concept.

The terminology used herein is for purposes of describing particular embodiments only and is not intended to be limiting. As used in the specification and appended claims, the singular forms of terms "a," "an" and "the" are intended to include both singular and plural forms, unless the context clearly dictates otherwise. Additionally, the terms "comprises," "comprising," and/or similar terms specify the presence of stated features, elements, and/or components, but do not preclude the presence or addition of one or more other features, elements, components, and/or groups thereof. As used herein, the term "and/or" includes any and all combinations of one or more of the associated listed items.

Unless otherwise noted, when an element or component is said to be "connected to," "coupled to," or "adjacent to" another element or component, it will be understood that the element or component can be directly connected or coupled to the other element or component, or intervening elements or components may be present. That is, these and similar terms encompass cases where one or more intermediate elements or components may be employed to connect two elements or components. However, when an element or component is said to be "directly connected" to another element or component, this encompasses only cases where the two elements or components are connected to each other without any intermediate or intervening elements or components.

The present disclosure, through one or more of its various aspects, embodiments and/or specific features or sub-components, is thus intended to bring out one or more of the advantages as specifically noted below. For purposes of explanation and not limitation, example embodiments disclosing specific details are set forth in order to provide a thorough understanding of an embodiment according to the present teachings. However, other embodiments consistent with the present disclosure that depart from specific details disclosed herein remain within the scope of the appended claims. Moreover, descriptions of well-known apparatuses and methods may be omitted so as to not obscure the description of the example embodiments. Such methods and apparatuses are within the scope of the present disclosure.

Generally, the various embodiments described herein provide an automated system for bringing together available techniques to present a healthcare knowledge graph for interventional procedures. The techniques are brought together via a deep learning algorithm that learns feature interactions across multiple images in order to figure out optimal graph connections using a graph neural network (GNN). That is, the GNN learns how various decision points (e.g., which tools to use) and image features (e.g., locations of lesions) affect each outcome. The optimal graph connections provide procedure workflows in real time that indicate next steps in the interventional procedure to produce optimal outcomes via the knowledge graph. The various embodiments may be implemented as a standalone controller or as a software feature in existing software or hardware that can access patient data, as discussed below.

The embodiments overcome challenges introduced by large amounts of image data generated during previous interventional procedures, and the difficulties in processing the image data to produce useful information in a timely manner. The embodiments may combine the structure of graphs with image data and other unstructured procedure information, such as patient health information (PHI) data, C-arm movement, user interface interaction, and devices used, for example, in order to figure out the connections between image features and procedural decisions that lead to an optimal outcome.

For example, the dual axis rotation provided by Xper-Swing, an image acquisition technique available on C-arm imaging systems available from Philips Healthcare, Best, The Netherlands, is difficult to plan and implement correctly and is therefore under used. However, it has been shown that this imaging technique reduces the amount of radiation exposure and contrast use. Therefore, the ability to suggest when this technique may be most beneficial may improve its usability. Using image data applied to a GNN to automatically provide suggestions to users (e.g., physicians) regarding next steps in the procedure, it may be suggested that using XperSwing may be most beneficial for treating patients with complex coronary anatomy. Another example is in lung lesion biopsy, where pulmonary lesions may require radial endobronchial ultrasound (R-EBUS) for lesion confirmation before a biopsy can be acquired, while other pulmonary lesions may not be suited for R-EBUS confirmation. Again, by using image data applied to a GNN and automatically providing feedback on the pulmonary lesions that will likely benefit from use of the R-EBUS confirmation procedure and the pulmonary lesions that will likely not benefit increases efficiency of performing the lung lesion biopsy procedure. For example, it helps to save time in trying to navigate an R-EBUS probe toward pulmonary lesions that ultimately will not benefit from the R-EBUS confirmation procedure. Another example is in cloud-based applications or pay-per-use applications, where such automated suggestions from image data applied to a GNN help to indicate which patients may benefit from the pay-per-use solutions or which hospitals may benefit from a subscription based on frequency of use of certain pay-per-use solutions or demographic information.

FIG. 1 is a simplified block diagram of a system for performing an interventional procedure on a subject, according to a representative embodiment.

Referring to FIG. 1, system includes a workstation 130 for implementing and/or managing the processes described herein. The workstation 130 includes one or more processors indicated by processing unit 120, one or more memories indicated by memory 140, interface 122 and display 124. The processing unit 120 may interface with an imaging system 160 through an imaging interface (not shown). The imaging system 160 may include one or more of any various types of medical imaging systems/modalities, including an X-ray imaging system, a CT imaging system, a magnetic resonance (MR) imaging system, a fluoroscopy imaging system, an angiography imaging system, a digitally subtracted angiography (DSA) imaging system, an ultrasound imaging system, an endoscopy imaging system, or a bronchoscopy imaging system, for example. Multiple types of imaging systems of the imaging system 160 may be used during the interventional procedure. For example, CT imaging may be used for locating and analyzing a treatment target in the subject 165, and an ultrasound imaging system may be used for guiding a medical instrument to the treatment target during the interventional procedure.

The memory 140 stores instructions executable by the processing unit 120. When executed, the instructions cause the processing unit 120 to implement one or more processes for performing an interventional procedure on a subject 165, described below. For purposes of illustration, the memory 140 is shown to include software modules, each of which includes the instructions corresponding to an associated capability of the system 100, as discussed below.

The processing unit 120 is representative of one or more processors or processing devices, and may be implemented by field programmable gate arrays (FPGAs), application specific integrated circuits (ASICs), a digital signal processor (DSP), a general purpose computer, a central processing unit, a computer processor, a microprocessor, a microcontroller, a state machine, programmable logic device, or combinations thereof, using any combination of hardware, software, firmware, hard-wired logic circuits, or combinations thereof. Any processing unit or processor herein may include multiple processors, parallel processors, or both. Multiple processors may be included in, or coupled to, a single device or multiple devices. The term "processor" as used herein encompasses an electronic component able to execute a program or machine executable instruction. A processor may also refer to a collection of processors within a single computer system or distributed among multiple computer systems, such as in a cloud-based or other multi-site application. Programs have software instructions performed by one or multiple processors that may be within the same computing device or which may be distributed across multiple computing devices.

The memory 140 may include main memory and/or static memory, where such memories may communicate with each other and the processing unit 120 via one or more buses. The memory 140 may be implemented by any number, type and combination of random access memory (RAM) and read-only memory (ROM), for example, and may store various types of information, such as software algorithms, artificial intelligence (AI) machine learning models, and computer programs, all of which are executable by the processing unit 120. The various types of ROM and RAM may include any number, type and combination of computer readable storage media, such as a disk drive, flash memory, an electrically programmable read-only memory (EPROM), an electrically erasable and programmable read only memory (EEPROM), registers, a hard disk, a removable disk, tape, compact disk read only memory (CD-ROM), digital versatile disk (DVD), floppy disk, Blu-ray disk, a universal serial bus (USB) drive, or any other form of storage medium known in the art. The memory 140 is a tangible storage medium for storing data and executable software instructions, and is non-transitory during the time software instructions are stored therein. As used herein, the term "non-transitory" is to be interpreted not as an eternal characteristic of a state, but as a characteristic of a state that will last for a period. The term "non-transitory" specifically disavows fleeting characteristics such as characteristics of a carrier wave or signal or other forms that exist only transitorily in any place at any time. The memory 140 may store software instructions and/or computer readable code that enable performance of various functions. The memory 140 may be secure and/or encrypted, or unsecure and/or unencrypted.

The system 100 also includes databases for storing information that may be used by the various software modules of the memory 140, including a picture archiving and communication systems (PACS) database 112 and a clinical database 116. The clinical database 116, in particular, generally refers to one or more databases storing patients' clinical information, such as electronic health record (EHR) data. Examples of clinical databases include EHR databases, radiological information system (RIS) databases, data warehouses, data repositories, and the like. The PACS database 112 and the clinical database 116 may be implemented by any number, type and combination of RAM and ROM, for example. The various types of ROM and RAM may include any number, type and combination of computer readable storage media, such as a disk drive, flash memory, EPROM, EEPROM, registers, a hard disk, a removable disk, tape, CD-ROM, DVD, floppy disk, Blu-ray disk, USB drive, or any other form of storage medium known in the art. The databases are tangible storage mediums for storing data and executable software instructions and are non-transitory during the time data and software instructions are stored therein. The databases may be secure and/or encrypted, or unsecure and/or unencrypted. For purposes of illustration, the PACS database 112 and the clinical database 116 are shown as separate databases, although it is understood that they may be combined, and/or included in the memory 140, without departing from the scope of the present teachings. The clinical database 116 may be built as a matter of routine at one or more facilities providing clinical care, storing at least patient demographic and clinical information.

The processing unit 120 may include or have access to an AI engine or module, which may be implemented as software that provides artificial intelligence, such as natural language processing (NLP) and machine learning algorithms, including graph neural network modeling, described herein. The AI engine may reside in any of various components in addition to or other than the processing unit 120, such as the memory 140, an external server, and/or cloud, for example. When the AI engine is implemented in a cloud, such as at a data center, for example, the AI engine may be connected to the processing unit 120 via the internet using one or more wired and/or wireless connection(s).

The interface 122 may be a user interface for providing information and data output by the processing unit 120 and/or the memory 140 to the user and/or for receiving information and data input by the user. That is, the interface 122 enables the user to enter data and to control or manipulate aspects of the processes described herein, and also enables the processing unit 120 to indicate the effects of the user's control or manipulation. All or a portion of the interface 122 may be implemented by a graphical user interface (GUI), such as GUI 128 viewable on the display 124, discussed below. The interface 122 may include one or more interface devices, such as a mouse, a keyboard, a trackball, a joystick, a microphone, a video camera, a touchpad, a touchscreen, voice or gesture recognition captured by a microphone or video camera, for example.

The display 124 may be a monitor such as a computer monitor, a television, a liquid crystal display (LCD), an organic light emitting diode (OLED), a flat panel display, a solid-state display, or a cathode ray tube (CRT) display, or an electronic whiteboard, for example. The display 124 includes a screen 126 for viewing internal images of a current subject (patient) 165 during an interventional procedure, as well as the GUI 128 to enable the user to interact with the displayed images and features during the interventional procedure.

Referring to the memory 140, current image module 141 is configured to receive and process a current image acquired of the current subject 165 by the imaging system 160 to provide current image data during the interventional procedure, in real time. The current image shows a treatment target in the subject. The current image data is provided to the display 124, so that the current image can be displayed and read/interpreted by the user while performing the interventional procedure.

Previous data module 142 is configured to receive and process previous data from previous interventional procedures of the same type as that currently being performed on the subject 165. The previous interventional procedures have been performed on several subjects, e.g., which may include the current subject 165, at the same and/or different facilities as the current interventional procedure. The previous data are used to train a deep learning graph neural network (GNN) model, discussed below. Generally, the more previous data available to the previous data module 142, the more reliable the output of the GNN model is when trained using the previous data.

The previous data includes previous image data from previous images acquired of subjects during the previous interventional procedures and corresponding previous treatment results. Like the current image, the previous images may have been acquired by any of a variety of imaging modalities. The previous images may include diagnostic (preoperative) images obtained prior to the respective previous interventional procedures, and interventional images acquired during the respective previous interventional procedures. The diagnostic images may be CT images and/or MR images, for example. The interventional images may be X-ray images, fluoroscopy sequences (e.g., including fluoroscopy sequences containing moving tools such as bronchoscopes, catheters, needles, and the like), angiography images, DSA images, ultrasound images, endoscopy images, and/or bronchoscopy images, for example. The previous images and/or the previous image data may be retrieved from an image database, such as the PACS database 112, for example. The previous data may also include unstructured procedure information corresponding to the previous image data. The unstructured procedure information may include PHI data (such as patient age, height, weight, patient history including smoking history, prior procedures, etc.), settings of the imaging system, such as C-arm movement or collimation settings of C-arm imaging systems (e.g., for X-ray imaging), used to acquire the previous images as well as user interface interactions, anesthesia administration, and devices used during previous interventional procedures in order to achieve previous treatment results.

In various embodiments, label data may be stored in association with the previous image data. The label data correspond to labels that indicate identified features or regions within the previous images that are relevant to a particular interventional procedure. The labels may be created manually or automatically, for example, using known automatic segmentation and/or automatic feature recognition techniques, and may be stored with the previous images in the same image database, such as the PACS database 112, or stored in a separate database, such as the clinical database 116, and associated with the previous images stored in another database.

The previous treatment results may include information indicating outcomes of the interventional procedures and/or outcomes at different phases of the interventional procedures (e.g., outcome of a device deployment step) with which the previous images are associated. The previous treatment results may include textual records associated with the previous image data, such as EHR data and/or EHR reports and/or case reports, for example, retrieved from a records database, such as the clinical database 116, for example. For textual records associated with the previous image data, relevant textual features may extracted from text data and used during training of the GNN, discussed below, using one or more NLP algorithms. For example, for a lung lesion biopsy, a report may indicate the diagnostic yield of the biopsy (conclusive or not). In some cases, outcomes are scored. The previous treatment results may also include information obtainable from the previous images themselves. For example, in a mechanical thrombectomy procedure for ischemic stroke treatment, a thrombolysis in cerebral infarction (TICI) score is assigned to evaluate the amount of perfusion (blood flow) after clot removal. In this case, the score may be looked up, or the post-op image from which the score is computed may be used to calculate the score directly if only the image is available.

Neural network module 143 is configured to apply the current image data provided by the current image module 141 to a deep learning GNN model during the interventional procedure, and to output one or more preferred next steps for the interventional procedure. The GNN model has been trained using the previous data provided by the previous data module 142, discussed below. The GNN model may be any compatible type of graph neural network capable of deep learning, such as a spatial convolutional network (similar to the general convolutional neural network (CNN)) model, a spectral convolutional network, a recurrent graph neural network (similar to the general recurrent neural network (RNN)) model, or a graph transformer network (similar to the general transformer network) model, for example. When the previous data also includes the unstructured procedure information for training the GNN model, the neural network module 143 applies current unstructured procedure information along with the current image data to the deep learning GNN model during the interventional procedure. The current unstructured procedure information likewise may include PHI data, current settings of the imaging system used to acquire the current image, as well as user interface interactions, anesthesia administration, and devices used during the interventional procedure.

Training module 144 is configured to train the GNN model to be applied by the neural network module 143 using the previous data provided by the previous data module 142, including the previous image data and the corresponding previous treatment results. The training causes the GNN model to provide a knowledge graph that includes feature representations corresponding to features of the previous interventional procedures and connections among the feature representations. That is, the GNN model receives feature representations from the previous image data, including treatment targets (e.g., lesion, aneurysm, stenosis, etc.), along with the previous treatment results, and builds the knowledge graphs to explore how the feature representations interact across the graph structure of the knowledge graph. The knowledge graph includes connections between feature representations to indicate the interactions. The GNN model may also receive unstructured procedure information or feature representations from unstructured procedure information which may be associated or combined with feature representations from the previous image data by, for instance, concatenating the (feature representations from) unstructured procedure information to feature representations from the previous image data. The knowledge graph then learns connections between feature representations additionally informed by unstructured procedure information. Alternatively, unstructured procedure information may be associated with feature representations from the previous image data simply by saving associated headers or metadata, for instance. In this case, the connections learned by the knowledge graph are not additionally informed by the unstructured procedure information, but the unstructured procedure information may be looked up as data associated with feature representations. For instance, users may look up metadata to decide which C-arm angle to use for the suggested next step.

For example, training the GNN model may include condensing the previous data from the previous data module 142 into feature representations (reduced dimensions), and learning the connections among feature representations using the previous image data and the corresponding previous treatment results. Condensing the previous data includes image feature extraction from the previous image data and word extraction from the previous treatment results, where image features and words may be extracted manually or automatically using methods like bag of features or bag of words to identify key features or key words indicating symptom, diagnosis, medication, procedure, and the like. Image features may be extracted using various image processing techniques like edge detection, feature segmentation, and the like. The image feature and word extractions may be performed with any type of neural networks with task-oriented outputs, like edge detection and feature segmentation (e.g., CNN, RNN, transformer networks) or neural networks with reconstruction-oriented outputs (e.g., encoder-decoder networks, variational encoder-decoder networks). The word extractions, in particular, may be performed using one or more NLP algorithms that include word embedding technology to extract relevant text from the contents of textual records, such as PHI data, EHR data, EHR reports and/or case reports, for example, by processing and analyzing natural language data. NLP is well known, and may include syntax and semantic analyses, for example, and deep learning for improving understanding with the accumulation of data, as would be apparent to one skilled in the art.

In some cases, multiple models may be used to learn feature representations targeted toward different regions of interest in the previous image data. Alternatively, a single model along with an attention mechanism may be used to semantically decouple a single feature representation into separate category- or label-related feature vectors representing different regions of interest. As stated above, the models learning feature representations may include CNN, RNN, encoder-decoder networks, and/or transformer network models, for example.

Once the feature representations have been learned, the next step is to learn the connections between different feature representations. Learning the connections between the feature representations may include initially assuming that all of the feature representations are connected by preliminary connections, and then training the GNN to estimate which of these preliminary connections are stronger, and identifying the stronger preliminary connections as the learned connections among the feature representations. The strength of a preliminary connection that yields a learned connection may be set using a predetermined strength threshold, for example.

Training the GNN model may provide a chain of inputs and outputs among the feature representations. For example, each feature representation may result in a classification output. The classification output may be an edge-level classification that represents the strength of a connection. For example, if a feature representation (node) has 10 edges, then the classification output may be a $10 \times 1$ vector, where each element of the vector represents a strength of connection across each edge connecting a feature representation to other feature representations. Therefore, the classification output informs a connection with another feature representation, which may in turn result in another classification output. In other words, an initial classification output provides an intermediate classification output, which may combine with subsequent inputs to inform further classification outputs as procedure progresses.

The GNN model is trained to provide classification outputs by adjusting the various parameters of the neural network including weights and biases such that when presented with input data, the neural network generates the expected output data. The adjusting of the parameters is informed by the value of a loss function. The loss may be computed by comparing the predicted classification with the ground truth classification from successful procedures. Loss functions that may be used to compute a value of the loss include negative log-likelihood, mean absolute error (or L1 norm), mean squared error, root mean squared error (or L2 norm), Huber loss, (binary) cross entropy loss, and so on, as would be apparent to one skilled in the art. Further, the loss for training the GNN model consists not only of a measure of whether a disease feature, for example, in a previous image resulted in the correct procedure suggestion or classification, but also whether the procedure suggestion or classification was optimal. For instance, a more invasive procedure may receive a higher penalty than a less invasive procedure if both procedures produce similar outcomes in a similar clinical scenario. During training, the value of the loss function is typically minimized and training is terminated when the value of the loss function satisfies one or more stopping criteria.

The feature representations of the knowledge graph may include at least one diagnostic feature representation of at least one pathological condition and at least one interventional or procedural feature representation for treating the at least one pathological condition during the interventional procedure. In various embodiments, the knowledge graph includes nodes corresponding to the feature representations and connections joining pairs of the nodes corresponding to the connections among the feature representations, respectively.

Figures 2, 3A, 3B:
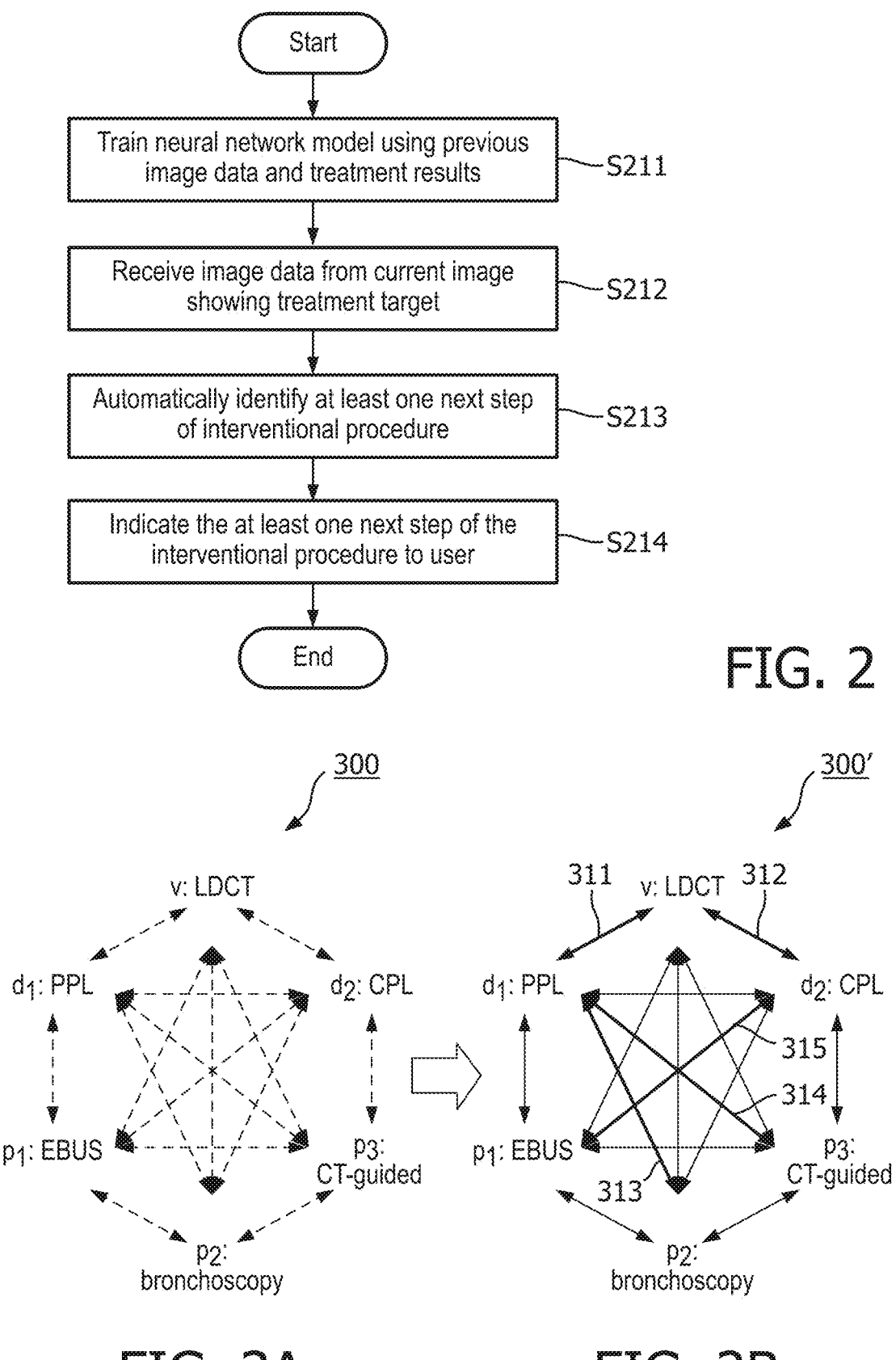
FIG. 2 is a flow diagram showing a method of performing an interventional procedure performed on a subject, according to a representative embodiment.
FIG. 3A shows an illustrative knowledge graph that includes examples of diagnostic feature representations and procedural feature representations, according to a representative embodiment.
FIG. 3B shows an illustrative knowledge graph that includes examples of diagnostic feature representations, procedural feature representations and corresponding connections, according to a representative embodiment.

FIGS. 3A and 3B show illustrative knowledge graphs that include examples of diagnostic feature representations, procedural feature representations, and corresponding connections, according to a representative embodiment. In particular, FIG. 3A shows a preliminary knowledge graph 300 that includes the diagnostic feature representations and the procedural feature representations, and preliminary connections assumed to exist between all of them, as indicted by dashed arrows. FIG. 3B shows a trained knowledge graph 300', derived from the preliminary knowledge graph 300, that includes the diagnostic feature representations, the procedural feature representations, and only connections between related ones of the diagnostic feature representations and procedural feature representations as determined by the training, as indicated by solid arrows.

In the example shown in FIGS. 3A and 3B, the interventional procedure to which the knowledge graphs 300 and 300' apply is a screening for potentially cancerous lung lesions, beginning with a low dose computed tomography (LDCT) image. The nodes of the knowledge graphs 300 and 300' include diagnostic feature representation v (patient visit) for the LDCT imaging, diagnostic feature representation d1 for peripheral pulmonary lesions (PPLs), and diagnostic feature representation d2 for central pulmonary lesions (CPLs), both of which may be potentially cancerous lung lesions. The nodes further include procedural feature representation p1 for endobronchial ultrasound (EBUS) guided biopsy procedure, procedural feature representation p2 for bronchoscopy-guided biopsy procedure, and procedural feature representation p3 for CT-guided biopsy procedure.

The training results in identification of various connections between the feature representations, as shown in FIG. 3B, where the connections may be referred to as classification outputs. For instance, the classification outputs may comprise a binary classification, where 0 indicates no connection and 1 indicates a connection. In the depicted example, the diagnostic feature representation v for the LDCT imaging has connection (classification output) 311 to the diagnostic feature representation d1 for a PPL and connection 312 to the diagnostic feature representation d2 for a CPL, meaning that the LDCT imaging results in identification of a PPL and/or a CPL. The diagnostic feature representation d1 for the identified PPL has connection 313 to the procedural feature representation p2 for the bronchoscopy-guided biopsy procedure and connection 314 to the procedural feature representation p3 for CT-guided biopsy procedure, meaning that these procedures are preferable for performing a biopsy on the PPL. The diagnostic feature representation d2 for the identified CPL has connection 315 to the procedural feature representation p1 for the EBUS-guided biopsy procedure, meaning that EBUS-guided biopsy is preferable for performing a biopsy on the CPL. Alternatively, the classification outputs may be continuous values between 0 and 1, higher values indicating stronger connections and lower values indicating weaker connections.

As mentioned above, the training may include a measure of whether a diagnostic feature representation resulted in the correct and optimal connection to a procedural feature representation. For example, referring again to FIG. 3B, similar image features for two separate instances of PPLs in the previous images resulted in a successful bronchoscopy-guided biopsy procedure for one instance and a successful CT-guided biopsy procedure for the other instance, indicated by the connections 313 and 314, respectively. The training also assigns the more invasive CT-guided biopsy procedure a higher penalty since the implication is that the less invasive bronchoscopy-guided biopsy procedure is able to produce a similar successful outcome. However, when the two similar image features resulted in an unsuccessful bronchoscopy-guided biopsy in one instance and a successful CT-guided biopsy procedure in the other instance, then the more invasive CT-guided biopsy procedure is not penalized. In this example, the GNN model learns the feature representations (e.g., the PPLs) that are optimally biopsied using the bronchoscopy-guided biopsy procedure and those that should not be biopsied using the bronchoscopy-guided biopsy procedure. Feature similarity may be computed during training by measuring the respective distances between the feature representations in feature space.

With regard to textual records associated with the previous interventional procedures, including the EHR data, EHR reports and/or case reports, relevant textual features are extracted from text data and used in the loss function to, for instance, weight or penalize the loss accordingly. The relevant textual features may be extracted using any compatible NLP algorithm, discussed above. The relevant textual features may be associated with the image features using any compatible association algorithm, such as text-to-image translation, for example. In this case, the training may use unlabeled data and learn associations to labels or keywords directly from associated texts by autoregressively modelling the textual features and image features as a single stream of data. For example, when image features indicate relatively strong connections for both the bronchoscopy-guided biopsy and the CT-guided biopsy for the subject, additional information about the subject suffering from chronic obstructive pulmonary disease (COPD), for example, would significantly weaken the connection to bronchoscopy-guided biopsy, making it clear that CT-guided biopsy is the optimal procedure for the subject.

Once the GNN model has been trained, the neural network module 143 is able to apply the trained GNN model to the current interventional procedure using the current image data from the current image module 141. The GNN model automatically outputs one or more preferred next steps for the interventional procedure while the interventional procedure is being performed to guide the user. More particularly, a current step of the interventional procedure corresponds to a current feature representation in the knowledge graph, such as the knowledge graph 300', provided by the training module 144. Each next step of the interventional procedure corresponds to a next feature representation in the knowledge graph, where the next step is connected to the current step by a connection. The connection between the current step and the next step identified by the GNN model is accentuated over the other connections to the current step by the GNN model. To the extent the knowledge graph is displayed, the accentuating may include visually highlighting the connection, e.g., using bold or dashed lines or different colors, to indicate the connection to the next step. To the extent the knowledge graph is not displayed, the accentuating may include simply identifying, displaying and/or storing the connection as having greater weight or significance than the other connections to the current step. For instance, the display may simply show a tabulated list of the identified next steps.

For example, the knowledge graph provided by the GNN model includes nodes and connections between the nodes, as discussed above. The GNN model receives a feature representation of the current image from the current image data of the subject 165 from the current image module 141, and identifies, based on the feature representation, a connection (classification output) to a target feature representation in the current image. For example, the GNN model may indicate connections to abnormalities in the current image of the patient 165, including lung lesions which may be cancerous, for example. Alternatively, the GNN model may indicate connections to the abnormalities through an interactive process, where the user selects margins of an apparent abnormality or designates a region of interest in the current image using the interface 122 and the GUI 128, and the GNN model in turn receives a feature representation of the identified margins or regions of interest from the current image and identifies, based on this feature representation, a connection to a target feature representation. In various embodiments, the abnormalities may be automatically detected using a segmentation algorithm, such as a U-Net, for example, or other automated techniques. For example, in FIG. 3B, the target feature representation may indicate a PPL identified in a current LDCT image of the subject's lung. The target feature node of the diagnostic feature representation d1 for the PPL is treated as the current step of the interventional procedure.

The GNN model analyzes application of the interventional procedure to the target feature representation based on various predetermined criteria, such as the size and location of the target feature, the type of interventional procedure being performed, the procedural tools available for the interventional process, and previous classifications and/or outcomes of the interventional procedure using the respective procedural tools. In various embodiments, the GNN model may apply any criteria relevant to analyzing application of the interventional procedure to the target feature representation, without departing from the scope of the present teachings. Additional criteria may be more subjective, such as the skill level of the user and the health of the subject.

Based on the analysis, the GNN model identifies the connection to the next step(s) in the interventional procedure that will most likely yield the best result (optimized result). In the knowledge graph, the next step is another node that is connected to the current node via a connection, where the connection is accentuated in the GNN model over other connections of the current node, as discussed above. For example, in FIG. 3B, the next steps for having identified a PPL in the current image are either performing a bronchoscopy-guided biopsy procedure indicated by the connection 313 or performing a CT-guided biopsy procedure indicated by the connection 314. The next step may be an intermediate step with regard to the overall interventional procedure. In this case, the identified next intermediate step (or intermediate feature representation) becomes the current step for purposes of determining another next indeterminate step or final step of the interventional procedure.

When there are multiple next steps available, the GNN model may assign weights to the possible next steps based on the training, to identify the best next step in view of the ultimate result. Generally, the next steps having higher probabilities of resulting in better outcomes have higher weights. The higher weights may be visualized by heavier bolding of the respective connections, for example. The next steps may be weighted the same or differently. When the next steps are weighted the same, it is up to the user to identify which next step to perform, e.g., based on additional factors that may not be considered by the GNN model, such as the extent of the user's personal experience in performing the respective procedures associated with the next steps. In an embodiment, the weighting assignment process may be tiered, where the GGN model determines weights according to a predetermined set of initial criteria, but then applies additional criteria, such as the level of skill of the user or the age/health of the subject, when the initial criteria provide multiple next steps having equal weights. When the next steps are weighted differently, the GNN model may automatically identify the next step with the highest weight as the next step in the interventional procedure. Of course, the user may override the automatic selection, and choose a next step with a lower weight, again based on additional factors that may not have been considered by the GNN model. The weighting may indicate confidence of each next step by the strength of the connection between the node indicating the current step and the node indicating the next step.

In an embodiment, the GNN model may use the connections of the knowledge graph to automatically perform procedure set up. On some C-arm imaging systems available from Philips Healthcare, Best, The Netherlands, for example, this may include automatic selection of appropriate Procedure Cards for the current interventional procedure. Procedure Cards offer presets consisting of standard procedure steps and clinical setups. These steps may be automatically populated based on the connections produced by the GNN. The appropriate Procedure Cards may be looked up on the C-arm imaging system equipped with Procedure Cards based on the procedure steps identified by the GNN, as would be apparent to one skilled in the art. The Procedure Cards indicate the optimal steps for the corresponding current interventional procedure.

In this embodiment, once a knowledge graph for a particular interventional procedure has been in use for a predetermined amount of time at a facility, then based on frequent strong connections in that knowledge graph, a subscription recommendation for a particular application for that interventional procedure may be made. For instance, if at a particular clinical site, the recommendation to perform lesion confirmation using an R-EBUS probe is often made during a lung nodule biopsy procedure, then the frequency of this recommendation may trigger a suggestion to purchase or subscribe to an application that, for instance, automatically identifies a lesion in a sequence of R-EBUS images. Recommendations may be made, for example, using simple post-processing processes, such as counting the frequency of particular recommendations, as would be apparent to one skilled in the art. Conversely, when a subscribed solution is not often recommended for a particular interventional procedure at a particular site, this may also be indicated.

The results of the applying the current image to the trained GNN are displayed on the display 124. Based on the displayed results, the user is able to see or determine the next steps of the interventional procedure. The next steps of the interventional procedure may then be implemented by the user. The GNN model continues to apply new current images during the interventional procedure so that next steps are updated, as needed. The next steps and the ultimate results for the subject 165 may be tracked so that they may be added to the PACS database 112 and the clinical database 116, and used for training the GNN model in the future.

In various embodiments, all or part of the processes provided by the neural network module 143 and/or the training module 144 may be implemented by an AI engine, for example. Also, training the GNN model and applying current image data to the trained GNN model to determine next steps of an interventional procedure in real time are not concepts that can be performed in the human mind.

FIG. 2 is a flow diagram of a method of performing an interventional procedure performed by a user on a subject, according to a representative embodiment. The method may be implemented by the system 100, discussed above, under control of the processing unit 120 executing instructions stored as the various software modules in the memory 140, for example.

Referring to FIG. 2, the method includes training a GNN model using previous data from previous interventional procedures in block S211. The previous data includes previous image data from previous images obtained during the previous interventional procedures and corresponding previous treatment results. The previous image data and the corresponding previous treatment results used for training the GNN model are obtained from a large set of previous interventional procedures, e.g., numbering in the thousands. The previous data may further include unstructured procedure information also corresponding to the previous images, in which case the GNN model may be further trained using the unstructured procedure information.

In block S212, current image data from a current image is received, where the current image shows a treatment target in the subject acquired by an interventional imaging system during the interventional procedure. The current image may be any compatible medical image provided by a corresponding imaging system, such as an X-ray image, a CT image, a fluoroscopy image, an angiography image, a DSA image, an ultrasound image, an endoscopy image, or a bronchoscopy image, for example. Feature representations of the current image are computed from the current image data, e.g., as described above. When the previous data also includes the unstructured procedure information for training the GNN model in block S211, the feature representations of the current image may be further computed from current unstructured procedure information, along with the current image data, corresponding to the current image.

In block S213, at least one next step of the interventional procedure is automatically identified by applying the feature representations of the interventional image data to the trained GNN model in real time, during the interventional procedure. More particularly, the feature representations of the current image data are applied to a trained knowledge graph provided by the GNN model. The current step of the interventional procedure corresponds to a current feature representation in the knowledge graph, and each next step corresponds to a next feature representation in the knowledge graph, which is connected to the current feature representation by a connection (classification output). The connection between the current step and the identified next step is accentuated over the other connections to the current step by the GNN model to indicate the progression of the interventional procedure to the next step. As discussed above, when the knowledge graph is displayed, the accentuating may include visually highlighting the connection, e.g., using bold or dashed lines or different colors, to indicate the connection to the next step. When the knowledge graph is not displayed, the accentuating may include simply identifying, displaying, and/or storing the connection as having greater weight or significance than the other connections to the current step. For instance, the display may simply show a tabulated list of the identified next steps.

In block S214, the at least one next step of the interventional procedure is indicated to the user. For example, the at least one next step of the interventional procedure may be indicated by displaying the knowledge graph provided by the GNN model, e.g., on the display 124, and visually highlighting (i) a node corresponding to a feature representation of the current step, (ii) each node corresponding to the at least one feature representation of the at least one next step, and (iii) each highlighted connection that connects the node corresponding to the feature representation of the current step to each highlighted node corresponding to the at least one feature representation of the at least one next step. The knowledge graph may also include all possible connections between the nodes for informational purpose, although only the connections between the current step and the next step(s) will be visually accentuated for clarity. Also, the display may enable a zooming function such that the user may zoom in on relevant nodes and connections as the interventional procedure progresses. In alternative embodiments, the knowledge graph itself may not be displayed, in which case the GNN model may indicate the at least one next step of the interventional procedure by displaying on the display 124 the name of the at least one next step and/or the tools used to perform the at least one next step and/or the imaging system used to perform the at least one next step.

Figure 4:
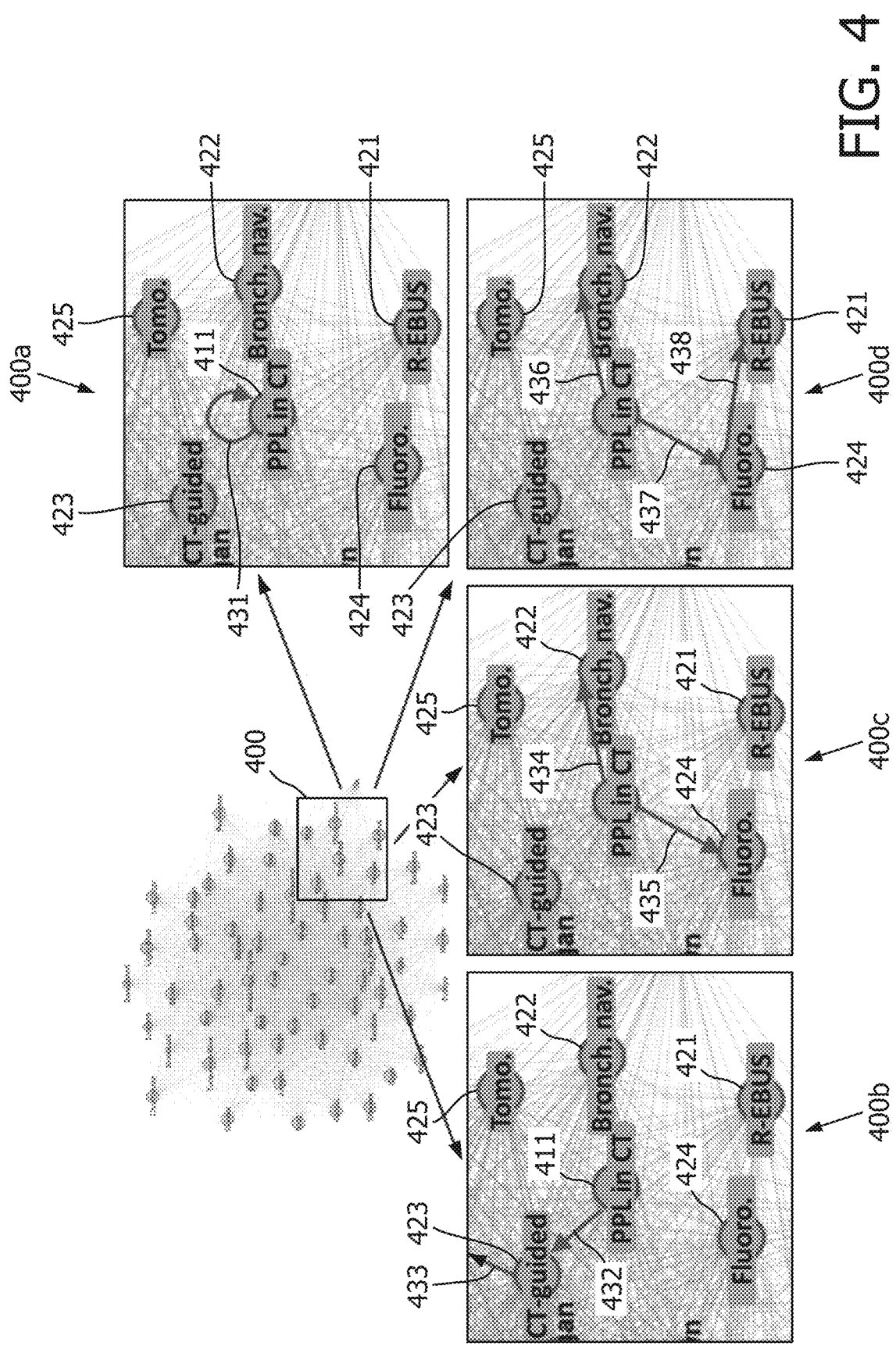
FIG. 4 shows a visualization of a knowledge graph from a trained GNN model and possible connections for identified feature representations, according to a representative embodiment.

An example of an interventional procedure on a subject according to the method described with reference to FIG. 2 is discussed below with reference to FIG. 4, which shows a visualization of a knowledge graph from a trained GNN model and all possible connections for the identified feature representations, according to a representative embodiment. The knowledge graph loosely corresponds to the knowledge graph shown in FIG. 3B, and involves an interventional procedure that screens for potentially cancerous lung lesions in the subject.

The interventional procedure begins with initially imaging the subject's lungs using a LDCT imaging, for example. FIG. 4 shows an area of interest 400 from the knowledge graph, and four scenarios shown by areas of interest 400a-400d in which the initial current images include a PPL under different circumstances leading to different sets of connections (classification outputs) among nodes corresponding to feature representations in the knowledge graph. The four scenarios each depict a feature representation of a PPL node 411 indicating a PPL identified (diagnosed) during the LDCT imaging. The PPL node 411 is connected to a number of nodes corresponding to feature representations indicating potential procedures as next steps for biopsying the PPL node as a result of training the GNN network model. In the depicted example, the treatment nodes include an R-EBUS node 421, a bronchoscopy-guided biopsy node 422 and a CT-guided biopsy node 423, discussed above, as well as a fluoroscopy-guided biopsy node 424 and a tomosynthesis node 425. The visualized knowledge graph shown in FIG. 4, including one or more of the areas of interest 4001-400d, may be displayed with corresponding highlighted connections, discussed below, on the display 124 during the interventional procedure.

In a first illustrative scenario corresponding to the area of interest 400a, the initial LDCT image shows that the PPL indicated by the PPL node 411 is extremely small (e.g., less than about 5 mm) and difficult to biopsy. Accordingly, a connection 431 showing the PPL node 411 connected to itself is highlighted. This indicates that the preferred next step (optimal course of action) is to wait, re-image the PPL at a future date, and perform a biopsy at that time if the PPL is shown to have increased in size and/or become easier to biopsy.

Notably, for purposes of illustration in each of the areas of interest 400a-400d, the connections indicating the preferred next steps (e.g., connection 431) are accentuated by use of a bolded arrow. It is understood, however, that any type of accentuation, including dashed and/or different colored lines, may be incorporated to indicate the connections for the preferred next steps, without departing from the scope of the present teachings.

In a second illustrative scenario corresponding to the area of interest 400b, the initial LDCT image shows that the PPL indicated by the PPL node 411 is small (e.g., less than about 10 mm) and not close enough to any airway branches (e.g., which may vary based on circumstances) to guarantee success of an endobronchial procedure (e.g., a bronchoscopy-guided, fluoroscopy-guided or R-EBUS procedure). Accordingly, a connection 432 connecting the PPL node 411 to the CT-guided biopsy node 423 is highlighted, indicating that the preferred next step is to perform a CT-guided biopsy procedure. During the subsequent CT-guided biopsy procedure, representative features from one or more intra-procedural CT images may in turn indicate connections to other preferred next steps from the CT-guided biopsy node 423, which may include steps such as instructions (not shown) to continue inserting biopsy needle, reacquisition of a CT image to confirm whether the biopsy needle is in the PPL, instructions to retract the biopsy needle, and so on, as indicated by the open-ended connection 433 pointing out of the area of interest 400*b*.

In a third illustrative scenario corresponding to the area of interest 400*c*, the initial LDCT image shows that the PPL indicated by the PPL node 411 is small, but close enough to airway branches (e.g., which may vary based on circumstances) that success of an endobronchial procedure is probable. Accordingly, a first connection 434 connecting the PPL node 411 to the bronchoscopy-guided biopsy node 422 and a second connection 435 connecting the PPL node 411 to the fluoroscopy-guided biopsy node 424 are both highlighted, indicating equally preferred next steps to perform the endobronchial biopsy procedure since these two techniques are typically used in conjunction. In the depicted example, the connection to the R-EBUS node 421 is not highlighted even though R-EBUS is considered to be an endobronchial procedure. This is because the GNN model has determined that the PPL is far enough away from the airway branches that it may not be captured in the field of view of the R-EBUS probe, and thus use of R-EBUS may not add additional confidence in the success of the biopsy procedure. In some cases, a weaker connection (e.g., less bold) to the CT-guided biopsy node 423 may also be indicated, as a possible but less desirable next step, depending on various features.

In a fourth scenario, corresponding to the area of interest 400*d*, the initial LDCT image shows that the PPL indicated by the PPL node 411 is small, but close enough to airway branches (e.g., which may vary based on circumstances) that success of an endobronchial procedure is probable, including in this example the R-EBUS procedure. Accordingly, a first connection 436 connecting the PPL node 411 to the bronchoscopy-guided biopsy node 422 and a second connection 437 connecting the PPL node 411 to the fluoroscopy-guided biopsy node 424 are both highlighted, indicating equally preferred next steps to perform the endobronchial biopsy procedure since these two techniques are typically used in conjunction. In addition, a third connection 438 connecting the fluoroscopy-guided biopsy node 424 to the R-EBUS node 421 is highlighted indicating strong subsequent connection to use of R-EBUS to confirm the location of the PPL. In this case, the image features provided by imaging during the fluoroscopy-guided biopsy may indicate that the PPL is close enough to the airways to be captured in the field of view of the R-EBUS probe or may indicate that the PPL is not visible in fluoroscopy and, therefore, may require confirmation of the location of the PPL using R-EBUS, and thus the additional time and effort spent in confirming the location of the PPL in the R-EBUS image is valuable since it adds significant confidence in the success of the biopsy procedure. In some cases, the subsequent connection 438 connecting the fluoroscopy-guided biopsy node 424 to the R-EBUS node 421 may be weak at the start of the endobronchial procedure, but may become stronger as the bronchoscope is navigated closer to the PPL. It is to be noted that these are exemplary scenarios described to explain the function of the knowledge graph according to various embodiments, and the circumstances within which the various scenarios may be suggested is learned by the GNN model through its training in order to maximize positive outcome of interventions.

Image features from the R-EBUS confirmation procedure, in turn, may inform which biopsy tool is optimal for biopsying the PPL. Biopsy tools may include biopsy needles, brushes, and forceps, for example.

When the PPL is not close enough to the airways to be captured in the field of view of the R-EBUS probe, and fluoroscopy guidance on its own does not generate sufficient confidence in the success of the endobronchial procedure according to the weights of the connections in the GNN model, then the image features provided by the imaging during the fluoroscopy-guided biopsy procedure may be expected to indicate a strong connection to tomosynthesis confirmation of the biopsy needle in the PPL at tomosynthesis node 425. The tomosynthesis confirmation procedure uses a limited sweep tomosynthesis image acquisition to generate a 3D image. This can enable confirmation that the biopsy needle is in the PPL before the needle is retracted. When available on a pay-per-use basis, the user may use an indication of suggested tomosynthesis confirmation to decide whether it is valuable to pay for this solution for a particular subject patient.

In a fifth scenario (not shown), the initial LDCT image shows that the PPL is close to airway branches, but also riskily close to the pleura covering the lungs (e.g., less than about 30 mm), in which case it may be unclear whether a bronchoscopy-guided biopsy procedure or a CT-guided biopsy procedure is optimal. The feature representations may therefore indicate a strong connection to the CT-guided biopsy node 423 since it is generally safer, and a slightly weaker connection to either the bronchoscopy-guided biopsy node 422 with fluoroscopy and R-EBUS confirmation. In this case, since the connections indicating the two options are both relatively strong, the user may decide, e.g., based on experience and personal comfort level, whether to refer the patient to CT-guided biopsy procedure or pursue the riskier endobronchial procedures.

In an embodiment, the user may indicate certain nodes in the knowledge graph as unavailable, based on various circumstances, such as the unavailability of tools for the corresponding treatments. Indicating the unavailability of nodes effectively removes these nodes from the knowledge graph for inference purposes. In this case, the GNN model makes its best prediction in the absence of the unavailable nodes. For instance, in the case where the knowledge graph may normally indicate a strong connection to the R-EBUS node 421 for confirmation of the location of the PPL, when the user "turns off" the R-EBUS node 421, e.g., because the R-EBUS probe is not available or the user is not trained to use R-EBUS, then the knowledge graph may indicate a strong connection to tomosynthesis node 425 instead for confirmation that the biopsy needle is in the lesion.

Conversely, in an embodiment, the user may indicate preferences for particular nodes in the knowledge graph. For example, the user who has limited training on the R-EBUS confirmation procedure may indicate a preference for the tomosynthesis confirmation procedure. In this case, the GNN model factors in the preference, such that the knowledge graph indicates a strong connection to the tomosynthesis node 425 when connections to both R-EBUS node 421 and the tomosynthesis node 425 are of comparable strengths. The knowledge graph will only indicate a strong connection to R-EBUS node 421 when connection to R-EBUS node 421 is significantly stronger than the connection to the tomosynthesis node 524.

As another example, the interventional procedure is an endovascular procedure, such as a mechanical thrombectomy for removing a blood clot (thrombus) from the brain vasculature in ischemic stroke patients, for example. The GNN model may inform the optimal procedure for performing the thrombectomy based on live fluoroscopy, in a similar manner as the lung lesion biopsy procedures discussed above. The success of blood clot removal during the thrombectomy is highly dependent on the positioning of the delivery catheter with respect to the blood clot. The delivery catheter delivers either a stent retriever used to retrieve the blood clot from the vessel or an aspiration catheter used to aspirate the blood clot out of the vessel.

The GNN model may be trained on fluoroscopy sequences acquired as the delivery catheter is being positioned for the thrombectomy. While the delivery catheter is not in place, the GNN model indicates to the user to continue navigating toward the blood clot. As the delivery catheter gets close to the blood clot, the output of the GNN model depends in large part on the angle between the delivery catheter and the blood clot, as visible in the current fluoroscopy image. For example, when the catheter and blood clot form an acute angle in the current fluoroscopy image, then the GNN model indicates the use of the aspiration catheter for removing the blood clot, since GNN model has learned through training that acute angles are related to high rates of failure using the stent retrievers. When the angle between the delivery catheter and the blood clot is closer to 180 degrees in the fluoroscopy imaging, e.g., which may be achieved as the user continues to reposition the delivery catheter during the procedure, then the GNN model indicates the use of the stent retriever to remove the blood clot.

In an embodiment, the knowledge graphs provided by the GNN model may be used for the training of novice users, including trainees. For example, the GNN model may allow a novice user to make decisions with regard to next steps in an interventional procedure based on their observations of a current image, and then provide a knowledge graph indicating nodes at which their decisions differed from the preferred decisions computed by the knowledge graph. In addition, feature clusters may be examined manually by the novice user to associate trends associated with feature clusters indicating particular connections in the knowledge graph, such as distances of PPLs from airway branches. In this case, the novice user not only sees where errors occurred, but also receives feedback from the GNN model regarding why a particular connection was indicated by the knowledge graph to teach the novice user similar associations between image features and optimal outcomes. These associations enable the novice user to implement optimal decisions during subsequent interventional procedures when a trained knowledge graph may not be available.

In another embodiment, the knowledge graphs provided by the GNN model may be used for resource allocation. For example, in a case where two patients are scheduled for the same PPL biopsy interventional procedure at the same time, the strength of connections in the knowledge graph triggered by LDCT image features may be used to decide which of the two patients might benefit more from an R-EBUS confirmation procedure use when only one R-EBUS probe is available. Similarly, feature representations of a knowledge graph provided by a GNN model for an XperSwing procedure for performing coronary angiography may indicate which patient might benefit more from the procedure.

In accordance with various embodiments of the present disclosure, the methods described herein may be implemented using a hardware computer system that executes software programs stored on non-transitory storage mediums. Further, in an exemplary, non-limited embodiment, implementations can include distributed processing, component/object distributed processing, and parallel processing. Virtual computer system processing may implement one or more of the methods or functionalities as described herein, and a processor described herein may be used to support a virtual processing environment.

Although performing interventional procedures using a trained GNN model to identify next steps in real time has been described with reference to exemplary embodiments, it is understood that the words that have been used are words of description and illustration, rather than words of limitation. Changes may be made within the purview of the appended claims, as presently stated and as amended, without departing from the scope and spirit of interventional procedure optimization in its aspects. Also, although performing interventional procedures using a trained GNN model to identify next steps in real time has been described with reference to particular means, materials and embodiments, there is no intention to be limited to the particulars disclosed; rather the embodiments extend to all functionally equivalent structures, methods, and uses such as are within the scope of the appended claims.

The illustrations of the embodiments described herein are intended to provide a general understanding of the structure of the various embodiments. The illustrations are not intended to serve as a complete description of all of the elements and features of the disclosure described herein. Many other embodiments may be apparent to those of skilled in the art upon reviewing the disclosure. Other embodiments may be utilized and derived from the disclosure, such that structural and logical substitutions and changes may be made without departing from the scope of the disclosure. Additionally, the illustrations are merely representational and may not be drawn to scale. Certain proportions within the illustrations may be exaggerated, while other proportions may be minimized. Accordingly, the disclosure and the figures are to be regarded as illustrative rather than restrictive.

One or more embodiments of the disclosure may be referred to herein, individually and/or collectively, by the term "invention" merely for convenience and without intending to voluntarily limit the scope of this application to any particular invention or inventive concept. Moreover, although specific embodiments have been illustrated and described herein, it should be appreciated that any subsequent arrangement designed to achieve the same or similar purpose may be substituted for the specific embodiments shown. This disclosure is intended to cover any and all subsequent adaptations or variations of various embodiments. Combinations of the above embodiments, and other embodiments not specifically described herein, will be apparent to those skilled in the art upon reviewing the description.

The Abstract of the Disclosure is provided to comply with 37 C.F.R. § 1.72(b) and is submitted with the understanding that it will not be used to interpret or limit the scope or meaning of the claims. In addition, in the foregoing Detailed Description, various features may be grouped together or described in a single embodiment for the purpose of streamlining the disclosure. This disclosure is not to be interpreted as reflecting an intention that the claimed embodiments require more features than are expressly recited in each claim. Rather, as the following claims reflect, inventive subject matter may be directed to less than all of the features of any of the disclosed embodiments. Thus, the following claims are incorporated into the Detailed Description, with each claim standing on its own as defining separately claimed subject matter.

The preceding description of the disclosed embodiments is provided to enable any person skilled in the art to practice the concepts described in the present disclosure. As such, the above disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents and shall not be restricted or limited by the foregoing detailed description.

The invention claimed is:

1. A system for performing an interventional procedure, the system comprising:

an imaging system configured to acquire a current image of a treatment target during the interventional procedure;

a display; and a processor configured to:

receive a model comprising a knowledge graph representing the interventional procedure by a plurality of feature representations and connections among the plurality of feature representations, the model configured to select a connection from among connections, corresponding to procedure steps of the interventional procedure, for a feature representation in the knowledge graph;

identify a feature representation of the treatment target in the current image of a subject acquired by the imaging system during the interventional procedure;

apply the model to select a next procedure step in the interventional procedure based on the feature representation of the treatment target; and indicate on the display to a user a next step of the procedure steps of the interventional procedure.

2. The system of claim 1, wherein the processor is further configured to:

train the model, to generate the knowledge graph to represent the interventional procedure and to select from among connections for a feature representation in the knowledge graph, using previous image data, including treatment targets, from previous images obtained during previous interventional procedures and corresponding previous treatment results.

3. The system of claim 2, wherein:

the knowledge graph of the trained model includes a first feature representation corresponding to a current step in the interventional procedure and at least one connection from the first feature representation to at least one second feature representation corresponding to at least one possible next step in the interventional procedure; and the model is trained to select a connection of the at least one connection connected to a second feature representation corresponding to a best next step of the interventional procedure based on the treatment target.

4. The system of claim 2, wherein the processor is further configured to:

train the model to assign weights to connections in the knowledge graph and to select from among the connections based on the assigned weights.

5. The system of claim 2, wherein the processor is further configured to train the model to select from among connections in the knowledge graph based on criteria associated with the interventional procedure.

6. The system of claim 5, wherein the criteria associated with the interventional procedure includes at least one of: size of the treatment target, location of the treatment target, type of the interventional procedure, procedural tools available for performing the interventional procedure, or previous classifications or outcomes of the interventional procedure using the procedural tools.

7. The system of claim 2, wherein the model is a graph neural network (GNN) model.

8. The system of claim 7, wherein the GNN model uses task-oriented outputs or reconstruction-oriented outputs to generate the plurality of feature representations in the knowledge graph.

9. The system of claim 2, wherein the model is trained using at least one of: (i) previous unstructured procedure information corresponding to the previous images obtained during the previous interventional procedures and (ii) current unstructured procedure information corresponding to the current image.

10. The system of claim 2, wherein the model is trained using the previous image data and the previous unstructured procedure information comprises concatenating the previous unstructured procedure information to feature representations from the previous image data.

11. The system of claim 2, wherein the model is trained by condensing the previous image data to provide the plurality of feature representations and learning the connections among the plurality of feature representations using the previous image data and the corresponding previous treatment results.

12. The system of claim 2, wherein the model is a graph neural network (GNN) model in which task-oriented outputs or reconstruction-oriented outputs are used to generate the plurality of feature representations in the knowledge graph.

13. The system of claim 1, wherein the plurality of feature representations comprise at least one diagnostic feature representation of at least one pathological condition and at least one procedural feature representation for treating the at least one pathological condition during the interventional procedure.

14. The system of claim 1, wherein the display includes a screen for viewing internal images of the subject during the interventional procedure and a GUI to enable the user to interact with the displayed images and features
during the interventional procedure.

15. A method for performing an interventional procedure, the method comprising:

acquiring from an imaging system a current image of a treatment target during the interventional procedure;

receiving a model comprising a knowledge graph representing the interventional procedure by a plurality of feature representations and connections among the plurality of feature representations, the model configured to select a connection from among connections, corresponding to procedure steps of the interventional procedure, for a feature representation in the knowledge graph;

identifying a feature representation of the treatment target in the current image of a subject acquired by the imaging system during the interventional procedure;

applying the model to select a next procedure step in the interventional procedure based on the feature representation of the treatment target; and indicating on a display to a user a next step of the procedure steps of the interventional procedure.

16. The method of claim 15, further comprising:

training the model, to generate the knowledge graph to represent the interventional procedure and to select from among connections for a feature representation in the knowledge graph, using previous image data, including treatment targets, from previous images obtained during previous interventional procedures and corresponding previous treatment results.

17. The method of claim 16, wherein:

the knowledge graph of the trained model includes a first feature representation corresponding to a current step in the interventional procedure and at least one connection from the first feature representation to at least one second feature representation corresponding to at least one possible next step in the interventional procedure; and the model is trained to select a connection of the at least one connection connected to a second feature representation corresponding to a best next step of the interventional procedure based on the treatment target.

18. The method of claim 16, wherein the model is trained to assign weights to connections in the knowledge graph and to select from among the connections based on the assigned weights.

19. The method of claim 16, wherein the model is trained to select from among connections in the knowledge graph based on criteria associated with the interventional procedure.

20. The method of claim 19, wherein the criteria associated with the interventional procedure includes at least one of: size of the treatment target, location of the treatment target, type of the interventional procedure, procedural tools available for performing the interventional procedure, or previous classifications or outcomes of the interventional procedure using the procedural tools.

* * * * *